United States Patent
Galbraith et al.

(10) Patent No.: US 11,324,904 B2
(45) Date of Patent: May 10, 2022

(54) POSITIVE AIRWAY PRESSURE SYSTEM WITH INTEGRATED OXYGEN

(71) Applicant: Separation Design Group LLC, Waynesburg, PA (US)

(72) Inventors: Stephen Douglas Galbraith, Waynesburg, PA (US); Robert M. Rauker, Plano, TX (US); Patrick J. Strollo, Gibsonia, PA (US)

(*) Notice: Subject to any disclaimer, the term of this patent is extended or adjusted under 35 U.S.C. 154(b) by 415 days.

(21) Appl. No.: 16/088,319

(22) PCT Filed: Mar. 24, 2017

(86) PCT No.: PCT/US2017/023990
§ 371 (c)(1),
(2) Date: Sep. 25, 2018

(87) PCT Pub. No.: WO2017/165749
PCT Pub. Date: Sep. 28, 2017

(65) Prior Publication Data
US 2019/0175856 A1   Jun. 13, 2019

Related U.S. Application Data

(60) Provisional application No. 62/313,186, filed on Mar. 25, 2016.

(51) Int. Cl.
*A61M 16/00* (2006.01)
*A61M 16/10* (2006.01)
(Continued)

(52) U.S. Cl.
CPC .............. *A61M 16/024* (2017.08); *A61B 5/08* (2013.01); *A61M 16/0063* (2014.02);
(Continued)

(58) Field of Classification Search
CPC .... A61M 16/024; A61M 16/12; A61M 16/16; A61M 16/0066; A61M 16/208;
(Continued)

(56) References Cited

U.S. PATENT DOCUMENTS 5,383,449 A   1/1995  Forare et al.
6,269,811 B1  8/2001  Duff et al.
(Continued)

FOREIGN PATENT DOCUMENTS

WO   WO-2011044091 A2 *  4/2011  ........ A61M 16/0672

OTHER PUBLICATIONS

Extended European Search Report dated Nov. 12, 2019 in EP Application No. 17771225.4.
(Continued)

*Primary Examiner* — Kendra D Carter
*Assistant Examiner* — Arielle Wolff
(74) *Attorney, Agent, or Firm* — Panitch Schwarze Belisario & Nadel LLP

(57) ABSTRACT

A device and a system that delivers continuous positive airway pressure in conjunction with oxygen delivery is disclosed. The system is portable so that patients may be mobile and conveniently travel. Several means are disclosed for integrating oxygen production into a positive airway pressure (PAP) device, including oxygen production machinery entirely integrated into the PAP housing, oxygen production machinery that mates with a PAP device but which may operate independently, and where portions of the oxygen production machinery are located in the PAP housing and other portions (for example, the compressor) are located in a separate module, such as, for example, an AC-to-DC power conversion module.

18 Claims, 14 Drawing Sheets

(51) Int. Cl.
| | |
|---|---|
| *A61B 5/08* | (2006.01) |
| *A61M 16/12* | (2006.01) |
| *A61M 16/16* | (2006.01) |
| *B01D 53/04* | (2006.01) |
| *A61M 16/20* | (2006.01) |
| *A61B 5/087* | (2006.01) |
| *A61M 16/06* | (2006.01) |

(52) U.S. Cl.
CPC ...... *A61M 16/0066* (2013.01); *A61M 16/101* (2014.02); *A61M 16/12* (2013.01); *A61M 16/16* (2013.01); *A61M 16/208* (2013.01); *B01D 53/0454* (2013.01); *A61B 5/087* (2013.01); *A61M 16/0069* (2014.02); *A61M 16/06* (2013.01); *A61M 16/109* (2014.02); *A61M 16/161* (2014.02); *A61M 16/20* (2013.01); *A61M 2016/0027* (2013.01); *A61M 2016/0033* (2013.01); *A61M 2202/0208* (2013.01); *A61M 2205/12* (2013.01); *A61M 2205/3351* (2013.01); *A61M 2205/3368* (2013.01); *A61M 2205/3553* (2013.01); *A61M 2205/3561* (2013.01); *A61M 2205/3584* (2013.01); *A61M 2205/3592* (2013.01); *A61M 2205/502* (2013.01); *A61M 2205/75* (2013.01); *A61M 2205/8206* (2013.01); *A61M 2205/8237* (2013.01); *A61M 2230/20* (2013.01); *A61M 2230/205* (2013.01); *A61M 2230/42* (2013.01); *A61M 2230/432* (2013.01); *B01D 53/04* (2013.01); *B01D 53/0415* (2013.01); *B01D 2259/455* (2013.01); *B01D 2259/4533* (2013.01)

(58) Field of Classification Search
CPC ............ A61M 16/0063; A61M 16/101; A61M 16/06; A61M 2205/12; A61M 2205/3584; A61M 2230/205; A61M 2205/3592; A61M 2016/0027; A61M 2205/8237; A61M 2016/0033; A61M 2202/0208; A61M 16/109; A61M 16/161; A61M 2205/3553; A61M 2205/3368; A61M 16/0069; A61M 2230/432; A61M 16/20; A61M 2205/3351; A61M 2205/502; A61M 2205/75; A61M 2230/20; A61M 2230/42; A61M 2205/3561; A61M 2205/8206; A61M 16/0057; A61B 5/08; A61B 5/087; B01D 53/0454; B01D 2259/4533; B01D 53/04; B01D 53/0415; B01D 2259/455

See application file for complete search history.

(56) References Cited

U.S. PATENT DOCUMENTS

| | | | |
|---|---|---|---|
| 6,551,384 B1* | 4/2003 | Ackley | B01D 53/0473 95/130 |
| 7,331,343 B2 | 2/2008 | Schmidt et al. | |
| 8,616,207 B2 | 12/2013 | Wilkinson | |
| 8,733,353 B2 | 5/2014 | Kramer et al. | |
| 8,888,902 B2 | 11/2014 | Galbraith et al. | |
| 8,894,751 B2 | 11/2014 | Galbraith et al. | |
| 9,199,055 B2 | 12/2015 | Galbraith et al. | |
| 9,592,361 B2 | 3/2017 | Mazela et al. | |
| 2005/0161043 A1* | 7/2005 | Whitley | B01D 53/0473 128/205.18 |
| 2006/0117957 A1 | 6/2006 | McCombs et al. | |
| 2006/0174871 A1* | 8/2006 | Jagger | A61M 16/101 128/201.25 |
| 2008/0302364 A1* | 12/2008 | Garde | A61M 16/201 128/204.23 |
| 2009/0107501 A1 | 4/2009 | Krieger | |
| 2010/0313898 A1* | 12/2010 | Richard | A61M 16/0858 128/848 |
| 2012/0055478 A1 | 3/2012 | Wilkinson | |
| 2012/0055480 A1 | 3/2012 | Wilkinson | |
| 2012/0055482 A1* | 3/2012 | Wilkinson | A61M 16/101 128/205.25 |
| 2012/0090611 A1* | 4/2012 | Graboi | A61M 16/1005 128/204.23 |
| 2013/0037027 A1* | 2/2013 | Schuller | A61M 16/0063 128/205.12 |
| 2013/0312757 A1* | 11/2013 | Cragg | A61M 16/0683 128/205.24 |
| 2014/0238398 A1* | 8/2014 | Christopher | A61M 16/0816 128/204.22 |
| 2016/0022951 A1 | 1/2016 | Galbraith | |
| 2016/0279362 A1* | 9/2016 | DeVries | A61M 16/0883 |
| 2017/0072159 A1 | 3/2017 | Romano et al. | |
| 2017/0113013 A1* | 4/2017 | Allum | B01D 53/0446 |

OTHER PUBLICATIONS

Int'l Search Report and Written Opinion dated Jul. 4, 2017 in Int'l Application No. PCT/US2017/023990.

Int'l Report on Patentability dated Sep. 25, 2018 in Int'l Application No. PCT/US2017/023990.

Office Action dated Dec. 12, 2021 in European Application No. 17771225.4.

* cited by examiner

POSITIVE AIRWAY PRESSURE SYSTEM WITH INTEGRATED OXYGEN

CROSS-REFERENCE TO RELATED APPLICATIONS

This application is a Section 371 of International Patent Application No. PCT/US2017/023990, filed Mar. 24, 2017 and titled, "Positive Airway Pressure System with Integrated Oxygen" and claims priority to U.S. Patent Application No. 62/313,186 filed Mar. 25, 2016, the entire contents of which are incorporated herein by reference.

FIELD OF THE INVENTION

The invention relates generally to devices, systems, and methods for continuous positive airway pressure in conjunction with oxygen delivery.

BACKGROUND OF THE INVENTION

Positive airway pressure (PAP) therapy is a mode of respiratory support used primarily to treat sleep apnea. PAP therapy is also used for those suffering respiratory failure or for newborn infants suffering from respiratory distress syndrome or bronchopulmonary dysplasia. There are, generally, two kinds of devices: bi-level positive airway pressure (BPAP) devices and continuous positive airway pressure (CPAP) devices. For both devices, therapy is provided via a device that increases the ambient air pressure and delivers it via tubing to a nasal or full face mask. In the case of BPAP devices, the pressure of the air coming from the device decreases when a patient breathes out. The therapy is typically provided when the patient is sleeping.

In some cases, additional cardiopulmonary conditions require that oxygen must be delivered concurrently with the CPAP or BPAP therapy. The oxygen source may be a cylinder of compressed oxygen, a cryogenic vessel, a stationary oxygen concentrator, or a portable oxygen concentrator. The additional equipment required to provide oxygen imposes an added expense and makes adhering to therapy, when traveling, difficult if not impossible. The World Health Organization estimates that approximately 300 million people have obstructive sleep apnea with 18 to 22 million of those people residing in the US. Of these, approximately 5 million people are using a PAP device, with an estimated 10% to 20% of these requiring adjunctive oxygen at some time during their therapy.

Presently, there a large number of PAP device manufacturers and the various designs have advantages regarding size, noise levels, sensitivity, cost, ease of transport, humidification capability, wireless communication, oximeter accessories and various other attributes that increase their usefulness. There are also a variety of mask designs that increase patient comfort.

When oxygen is required by a PAP user, a prescription is written for a certain oxygen flow that is to be added to the CPAP or BPAP delivered air. The oxygen delivery rate is an actual flow rate or a pulsed equivalent flow rate. The patient then purchases or rents the appropriate oxygen delivery system and the equipment needed to attach the oxygen source to the PAP device.

Typical limited portability oxygen concentrators, commonly referred to as "home" versions, weigh about 30 to 60 pounds, cost from about $1,500 to $3,000 and have a noise level from about 40 to 50 decibels. Portable oxygen concentrators are significantly smaller and lighter than home oxygen concentrators, but typically cost a thousand dollars more than the home version and do not produce as much oxygen. A third option for supplying oxygen is through the use of liquid or pressurized canisters or bottles. Liquid or pressurized oxygen is more expensive than the concentrators and have travel limitations. In addition, the pressurized cylinders needed for night time use can be quite large, being about 29 to 40 inches tall and weighing about 100 to 160 pounds. Some oxygen concentrators can weigh 30 pounds or more.

At the present time, there are no combination PAP plus oxygen therapy devices that are both portable and fully integrated into a single system. The invention is directed to these, as well as other, important needs.

BRIEF SUMMARY OF THE INVENTION

The invention provides a device and a system that delivers continuous positive airway pressure in conjunction with oxygen delivery. The system is portable so that patients may be mobile and conveniently travel. Several means may be used for integrating oxygen production into a positive airway pressure (PAP) device, including having the oxygen production machinery entirely integrated into the PAP housing, oxygen production machinery that mates with a PAP device but which may operate independently, and where portions of the oxygen production machinery are located in the PAP housing and other portions (for example, the compressor) are located in a separate module, such as, for example, an AC-to-DC power conversion module.

Accordingly, in one embodiment, the invention is directed to positive airway pressure systems, comprising:
- a controllable flow generator operable to provide breathable gas at a first pressure; wherein said first pressure is above atmospheric pressure;
- a gas delivery tube coupled to said controllable flow generator;
- a controllable oxygen concentrator device operable to provide oxygen-enriched gas;
- an enriched gas delivery tube coupled to said controllable oxygen concentrator device and connected to said controllable flow generator;
- a patient mask coupled to said gas delivery tube to receive breathable gas from said flow generator and to provide said gas, at a treatment pressure, to an airway of a patient;
- a controller operable to receive an input signal and to control the magnitude of said treatment pressure provided by said flow generator; and
- sensor to detect patient respiratory airflow and to generate an input signal to said controller.

In another embodiment, the invention is directed to positive airway pressure systems, comprising:
- a controllable flow generator operable to provide breathable gas at a first pressure;
- wherein said first pressure is above atmospheric pressure; and
- wherein said controllable oxygen concentrator device comprises at least one user-replaceable sieve cartridge comprising less than about 50 g adsorbent;
- a gas delivery tube coupled to said controllable flow generator;
- a controllable oxygen concentrator device operable to provide oxygen-enriched gas;
- an enriched gas delivery tube coupled to said controllable oxygen concentrator device and connected to said controllable flow generator;

a patient mask coupled to said gas delivery tube to receive breathable gas from said flow generator and to provide said gas, at a treatment pressure, to an airway of a patient;
a controller operable to receive an input signal and to control the magnitude of said treatment pressure provided by said flow generator; and
sensor to detect patient respiratory airflow and to generate an input signal to said controller.

In a further embodiment, the invention is directed to positive airway pressure systems, comprising:
a first module comprising:
a controllable flow generator operable to provide breathable gas at a first pressure; wherein said first pressure is above atmospheric pressure;
a gas delivery tube coupled to said controllable flow generator;
a patient mask coupled to said gas delivery tube to receive breathable gas from said flow generator and to provide said gas, at a treatment pressure, to an airway of a patient;
a controller operable to receive an input signal and to control the magnitude of said treatment pressure provided by said flow generator; and
a sensor to detect patient respiratory airflow and to generate an input signal to said controller;
a second module;
wherein said second module is a battery or a charger;
and a third module comprising:
a controllable oxygen concentrator device operable to provide oxygen-enriched gas;
an enriched gas delivery tube coupled to said controllable oxygen concentrator device and connected to said controllable flow generator;
wherein said third module is mateable with said first module, said second module, or both said first module and said second module.

In another embodiment, the invention is directed to positive airway pressure systems, comprising:
a first module comprising:
a controllable flow generator operable to provide breathable gas at a first pressure;
wherein said first pressure is above atmospheric pressure; and
wherein said controllable oxygen concentrator device comprises at least one user-replaceable sieve cartridge comprising less than about 50 g adsorbent;
a gas delivery tube coupled to said controllable flow generator;
a patient mask coupled to said gas delivery tube to receive breathable gas from said flow generator and to provide said gas, at a treatment pressure, to an airway of a patient;
a controller operable to receive an input signal and to control the magnitude of said treatment pressure provided by said flow generator; and
a sensor to detect patient respiratory airflow and to generate an input signal to said controller;
a second module;
wherein said second module is a battery or a charger;
and a third module comprising:
a controllable oxygen concentrator device operable to provide oxygen-enriched gas;
an enriched gas delivery tube coupled to said controllable oxygen concentrator device and connected to said controllable flow generator;
wherein said third module is mateable with said first module, said second module, or both said first module and said second module.

BRIEF DESCRIPTION OF THE SEVERAL VIEWS OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE INVENTION

Definitions

Figure 1A:
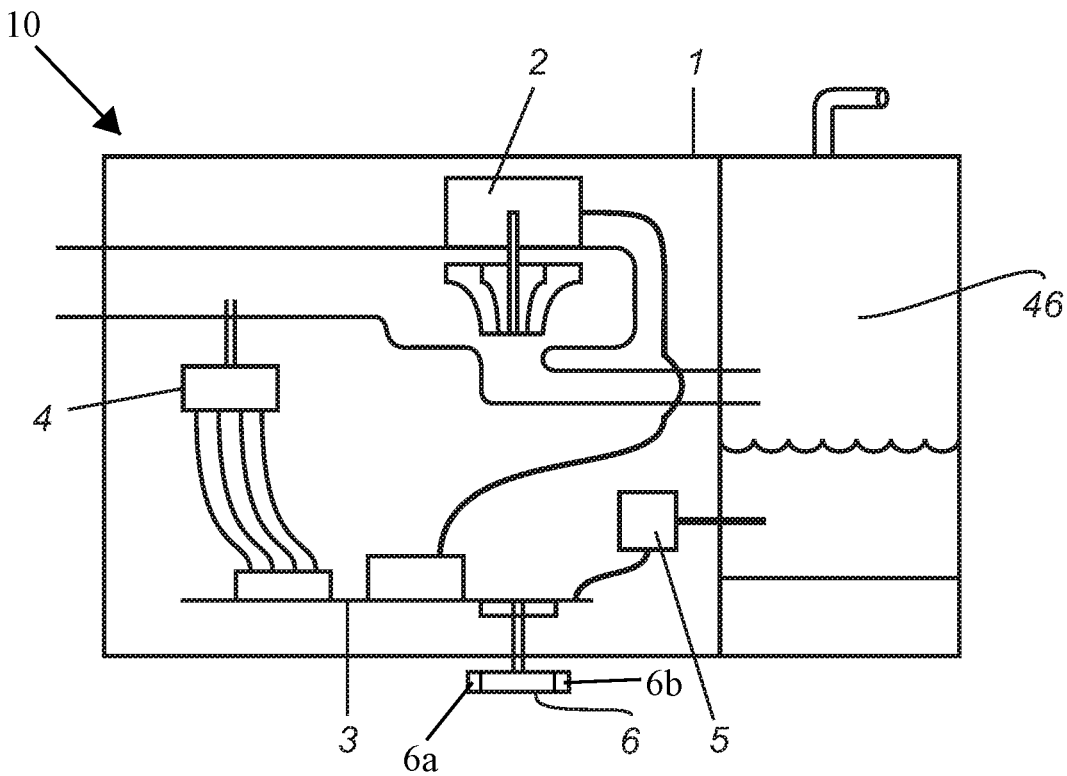
FIG. 1A is a cross-sectional view of a conventional positive airway pressure (PAP) machine 10 with a case or housing 1, a blower 2, and sensors, including a pressure sensor 4, and a temperature sensor 5.

The following definitions are provided for the full understanding of terms used in this specification.

As used herein, the article "a" means "at least one," unless the context in which the article is used clearly indicates otherwise.

As used herein, the terms "separation" and "separating" mean the act or process of isolating or extracting from or of becoming isolated from a mixture (a composition of two or more substances that are not chemically combined).

As used herein, the terms "purification" and "purifying" means the act or process of separating and removing from anything that which is impure or noxious, or heterogeneous or foreign to it.

As used herein, the term "fluid" refers to a continuous amorphous substance that tends to flow and to conform to the outline of its container, including a liquid or a gas, and specifically includes solutions (where solids dissolved in the liquid or gas) and suspensions (where solids are suspended in liquid or gas).

As used herein, the term "portable" refers to a device that may be capable of being carried or moved. Preferably, the term refers to a device that may be carried by an adult or child with little or no effort. However, the term also refers to a device that is not permanently affixed to a permanent structure and is of sufficiently low mass and bulk that it may be easily transported as part of a vehicle or transportation device. Preferably, the oxygen enrichment devices of the invention weigh less than about 1 kg.

As used herein, the term "chamber" refers to a three-dimensional volume having a generally solid outer surface that is generally elliptical or circular in cross-sectional shape.

As used herein, the term "adsorbent" or "adsorbent contactor" refers to an adsorbent or a membrane containing an adsorbent.

As used herein, the term "passageway" refers to a way through or along which a substance, such as a liquid, gas, or solid, may pass through one point to another, regardless of length. Examples of passageways include, without limitation, pipes, openings, conduits, and the like.

As used herein, the term "user-replaceable" with reference to sieve cartridges or modules, therapeutic cartridges, or other component parts, refers to a part or module that it is easily removed and changed by a non-technical person, including the patient, family member, or caregiver, where the person may have diminished physical capabilities, using no special tools and requiring no specialized expertise or assistance from manufacturer, distributor, or technical expert.

Reference will now be made in detail to the preferred embodiments of the invention, examples of which are illustrated in the drawings and the examples. This invention may, however, be embodied in many different forms and should not be construed as limited to the embodiments set forth herein. In addition and as will be appreciated by one of skill in the art, the invention may be embodied as a product, method, system or process.

The invention provides a device and a system that delivers continuous positive airway pressure in conjunction with oxygen delivery. The system is portable so that patients may be mobile and conveniently travel. For instance, it may be transported as "carry on luggage" on an airplane. Several means may be used for integrating oxygen production into a positive airway pressure (PAP) device, including oxygen production machinery (machinery that separates oxygen from air) entirely integrated into the PAP housing, oxygen production machinery that mates with a PAP device but which may operate independently, and where portions of the oxygen production machinery are located in the PAP housing and other portions (for example, the compressor) are located in a separate module, such as, for example, an AC-to-DC power conversion module.

Accordingly, in one embodiment, the invention is directed to positive airway pressure systems, comprising:
  a controllable flow generator 10*a* operable to provide breathable gas at a first pressure; wherein said first pressure is above atmospheric pressure;
  a gas delivery tube 13 *a* coupled to said controllable flow generator 10*a*;
  a controllable oxygen concentrator device 11 operable to provide oxygen-enriched gas;
  an enriched oxygen delivery hose 17 coupled to said controllable oxygen concentrator device 11 and connected to said controllable flow generator 10*a*;
  a patient mask 13 coupled to said gas delivery tube 13*a* to receive breathable gas from said flow generator 10*a* and to provide said gas, at a treatment pressure, to an airway of a patient;
  a controller or controls 6 operable to receive an input signal and to control the magnitude of said treatment pressure provided by said flow generator 10*a*; and
  a sensor 13*b* to detect patient respiratory airflow and to generate an input signal to said controller 6.

In another embodiment, the invention is directed to positive airway pressure systems, comprising:
  a controllable flow generator 10*a* operable to provide breathable gas at a first pressure; wherein said first pressure is above atmospheric pressure;
  wherein said controllable oxygen concentrator device 11 comprises at least one user-replaceable sieve cartridge 15 comprising less than about 50 g adsorbent;
  a gas delivery tube 13 *a* coupled to said controllable flow generator 10*a*;
  a controllable oxygen concentrator device 11 operable to provide oxygen-enriched gas;
  an enriched oxygen delivery hose 17 coupled to said controllable oxygen concentrator device 11 and connected to said controllable flow generator 10*a*;
  a patient mask 13 coupled to said gas delivery tube 13*a* to receive breathable gas from said flow generator 10*a* and to provide said gas, at a treatment pressure, to an airway of a patient;

a controller or controls 6 operable to receive an input signal and to control the magnitude of said treatment pressure provided by said flow generator 10a; and a sensor 13b to detect patient respiratory airflow and to generate an input signal to said controller 6.

In a further embodiment, the invention is directed to positive airway pressure systems, comprising:

a first module comprising:

a controllable flow generator 10a operable to provide breathable gas at a first pressure; wherein said first pressure is above atmospheric pressure;

a gas delivery tube 13a coupled to said controllable flow generator 10a;

a patient mask coupled to said gas delivery tube to receive breathable gas from said flow generator and to provide said gas, at a treatment pressure, to an airway of a patient;

a controller or controls 6 operable to receive an input signal and to control the magnitude of said treatment pressure provided by said flow generator 10a; and a sensor 13b to detect patient respiratory airflow and to generate an input signal to said controller 6;

a second module;

wherein said second module is a battery or a charger 31; and a third module comprising:

a controllable oxygen concentrator device 11 operable to provide oxygen-enriched gas;

an enriched oxygen delivery hose 17 coupled to said controllable oxygen concentrator device 11 and connected to said controllable flow generator 10a;

wherein said third module is mateable with said first module, said second module, or both said first module and said second module.

As used herein, "mateable" includes the proper alignment and removable connection of the pneumatic and electrical connections of the various modules.

In another embodiment, the invention is directed to positive airway pressure systems, comprising:

a first module comprising:

a controllable flow generator 10a operable to provide breathable gas at a first pressure;

wherein said first pressure is above atmospheric pressure; and wherein said controllable oxygen concentrator device 11 comprises at least one user-replaceable sieve cartridge 15 comprising less than about 50 g adsorbent;

a gas delivery tube 13a coupled to said controllable flow generator 10a;

a patient mask coupled to said gas delivery tube to receive breathable gas from said flow generator and to provide said gas, at a treatment pressure, to an airway of a patient;

a controller or controls 6 operable to receive an input signal and to control the magnitude of said treatment pressure provided by said flow generator 10a; and a sensor 13b to detect patient respiratory airflow and to generate an input signal to said controller;

a second module;

wherein said second module is a battery or a charger 31; and a third module comprising:

a controllable oxygen concentrator device 11 operable to provide oxygen-enriched gas;

an enriched oxygen delivery hose 17 coupled to said controllable oxygen concentrator device 11 and connected to said controllable flow generator 10a;

wherein said third module is mateable with said first module, said second module, or both said first module and said second module.

In certain embodiments, said gas delivery tube 13a and said enriched gas delivery tube 17 terminate in said patient mask 13. This arrangement minimizes the dilution of oxygen-enriched gas to the patient during inhalation. In certain embodiments, at least a portion of said gas delivery tube 13a and at least a portion of said enriched gas delivery tube 17 are co-axially oriented, as a tube within a tube (See FIG. 4 with the gas delivery tube 13a and the enriched gas delivery tube 17 shown in solid linetype). In certain embodiments, the central axis of at least a portion of said gas deliver tube 13a and the central axis of at least a portion of said enriched gas delivery tube 17 are substantially parallel forming a dual, side-by-side lumen (See FIG. 4 with the gas delivery tube 13a and the enriched gas delivery tube 17 shown in dashed linetype).

In certain embodiments, the positive airway pressure system of the invention further comprises at least one battery 24. In certain embodiments, the positive airway pressure system of the invention further comprises a charger 31 for said at least one battery 24.

In certain embodiments, the positive airway pressure system of the invention further comprises at least one AC to DC power supply. In certain embodiments, the positive airway pressure system of the invention further comprises a AC to DC power supply for said controllable flow generator 10a. In certain embodiments, the positive airway pressure system of the invention further comprises a AC to DC power supply for said controllable oxygen concentrator device 11.

In certain embodiments, the positive airway pressure system of the invention further comprises a conserver 14.

In certain embodiments, said controllable oxygen concentrator device is housed in a separate module from said controllable flow generator 10a. In certain embodiments, said controllable oxygen concentrator device 11 is housed in the same module as said controllable flow generator 10a. In certain embodiments, said controllable oxygen concentrator device 11 comprises a linear compressor.

In certain embodiments, the positive airway pressure system of the invention further comprises a wireless transmitter 6a or receiver 6b or both a transmitter 6a and receiver 6b. The wireless transmitter 6a or receiver 6b may employ electromagnetic wireless technologies, such as radio, light (such as, for example, infrared), magnetic, and/or electric fields or the use of sound. The wireless transmitter 6a or receiver 6b may use Bluetooth technology. The wireless transmitter 6a may be used to communicate information regarding system operation and/or to show whether or not the patent is complying with the therapy regime. The wireless receiver 6b may be used to receive information to adjust parameters of operation.

In certain embodiments, the positive airway pressure system of the invention further comprises a receptacle 51 for a user-replaceable therapeutic cartridge 50.

In certain embodiments, the positive airway pressure system of the invention further comprises:

a user-replaceable therapeutic cartridge 50; and a receptacle 51 for said user-replaceable therapeutic cartridge 50.

The therapeutic cartridge 50 may contain any of a number of materials, including vaporizable or atomizable fluids, including, but not limited to antibiotics, antiallergic agents, bronchodilators, antihistamines, decongestants, inhaled corticosteroids, and the like.

In certain embodiments, the positive airway pressure system of the invention is light enough to be carried by a person, especially an elderly, disabled, or infirmed person, when moving or traveling. Preferably, the system weighs less than about 10 pounds, more preferably, less than about 8 pounds, even more preferably, less than about 6 pounds, and yet even more preferably, less than about 4 pounds.

In certain embodiments, said controllable oxygen concentrator device comprises at least one user-replaceable sieve cartridge. In certain embodiments, said user-replaceable sieve cartridge comprises at least two adsorbent beds. In certain embodiments, the adsorbent beds in each cartridge contain a total of less than about 50 g adsorbent.

In certain embodiments, the delivery rate of said oxygen-enriched gas is controlled by a medical professional, programmed into said system, dependent upon a breath analysis, dependent upon blood oximetry feedback, dependent upon a respiratory arrhythmia event, or a combination thereof.

Positive Airway Pressure System

Figure 1B:
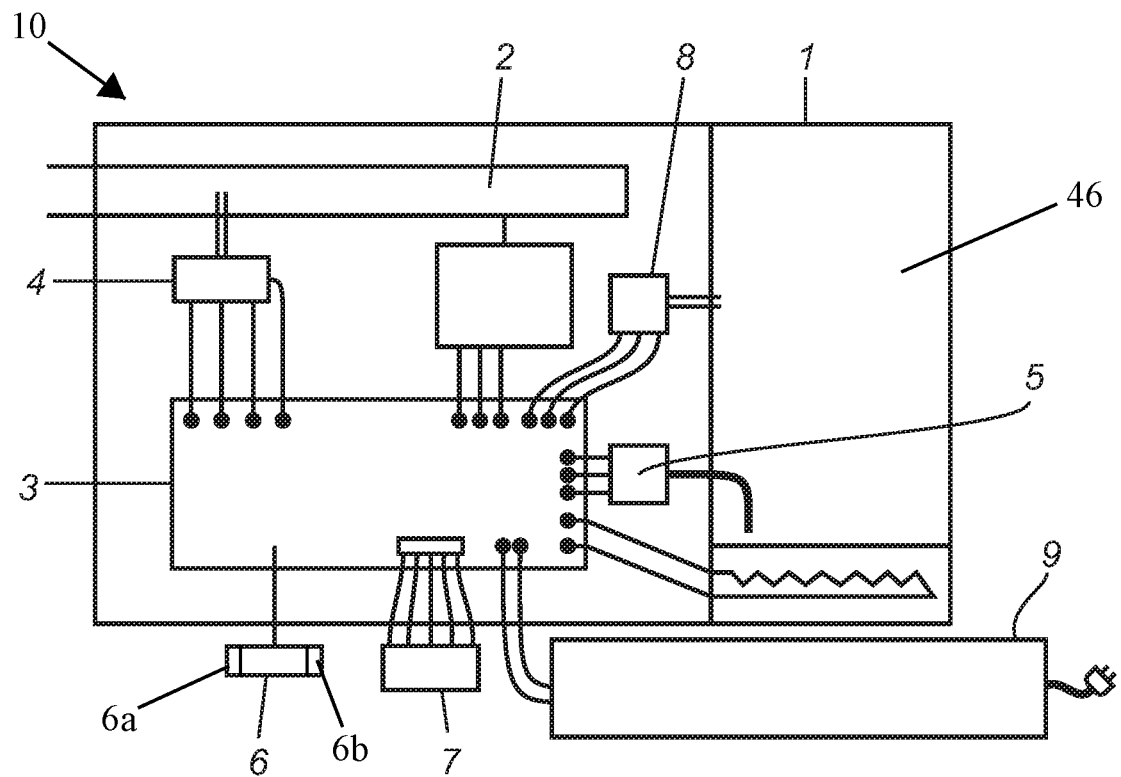
FIG. 1B is a schematic diagram of the machine shown in FIG. 1A.

A conventional PAP system consists of a housing, a power supply, a blower, a motor, a means for connection to a mask, electronic control means, and possibly a humidifier. These components are shown in FIGS. 1A and 1B.

Figure 2:
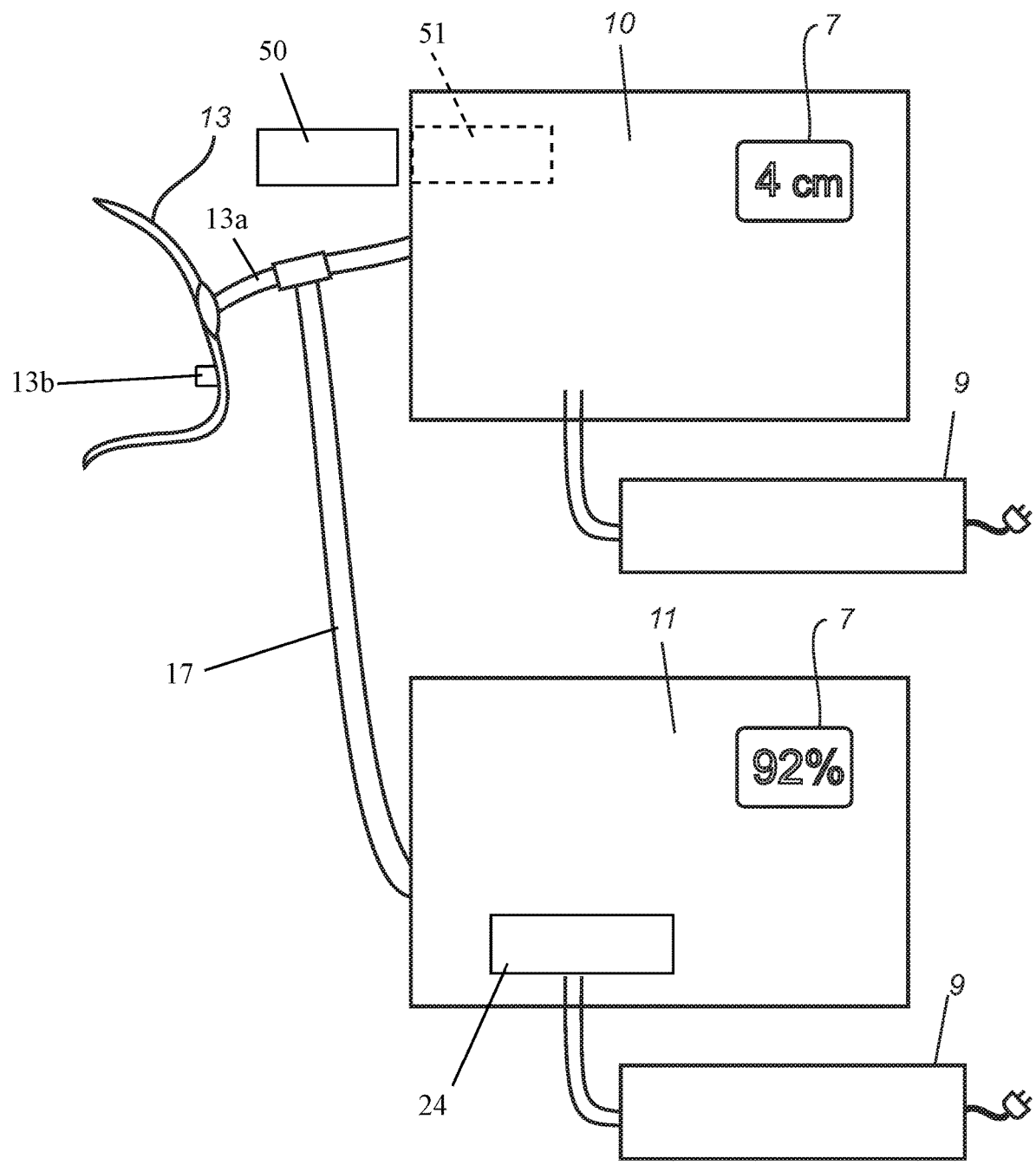
FIG. 2 illustrates how conventional PAP devices 10 are currently used in conjunction with oxygen concentrators 11.

A PAP machine of one embodiment of the invention is shown in FIG. 2 coupled to an oxygen source. In this case, the source is an oxygen concentrator. An oxygen concentrators typically employ pressure swing adsorption in an electrically powered system that removes nitrogen from air to deliver a >85% purity oxygen product. As FIG. 2 illustrates, the use of oxygen with PAP is not presently a convenient therapy for patients that require mobility and/or have the need to travel.

The invention preferably uses specialized adsorbents, rapid cycle times and user-replaceable sieve beds to provide oxygen concentrator components that are small enough to be integrated into a typical PAP machine format. 100-micron diameter sieve (adsorbent) beads can enable ultra rapid cycle times, as described in U.S. Pat. No. 8,894,751 which is incorporated herein by reference in its entirety. In the preferred embodiment, the amount of sieve material needed may be one-fifth to one-tenth that needed in standard oxygen concentrators having the same output. As an example, an existing concentrator having an output of 860 ml/minute of oxygen will have sieve columns occupying about 12 to 15 in$^3$. The sieve beds utilized in preferred embodiment of the invention produce >800 ml/min of oxygen yet occupy a volume of less than 2 in$^3$.

Figure 3:
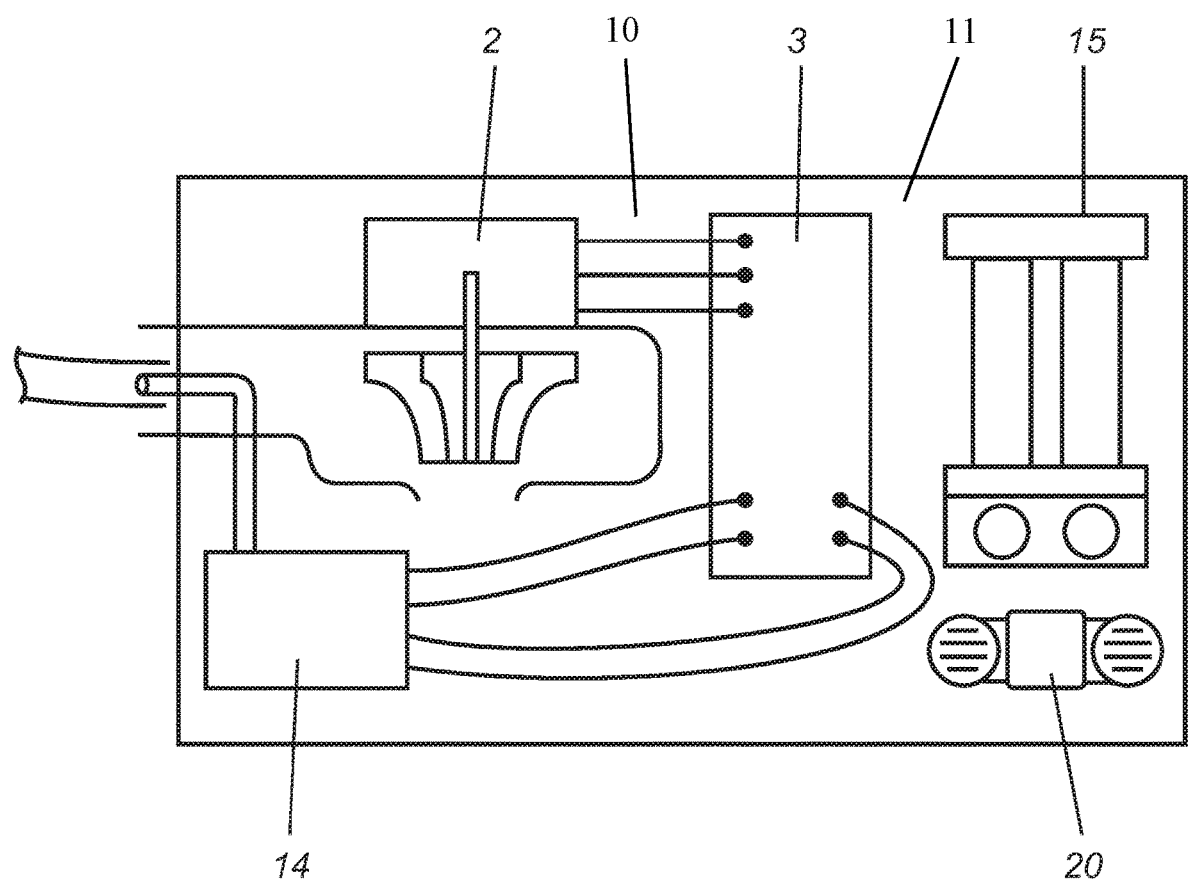
FIG. 3 shows how a user-replaceable sieve module 15 and valve manifold can be situated in a PAP device or system in one embodiment.

It is only by the use of this miniaturized oxygen generation technology that a truly portable PAP and oxygen device is made possible. FIG. 3 shows one method of placing the oxygen concentrating components in a PAP machine. The alterations to the PAP machine are not significant and do not impede portability or change how the patient interacts with the device.

Figure 4:
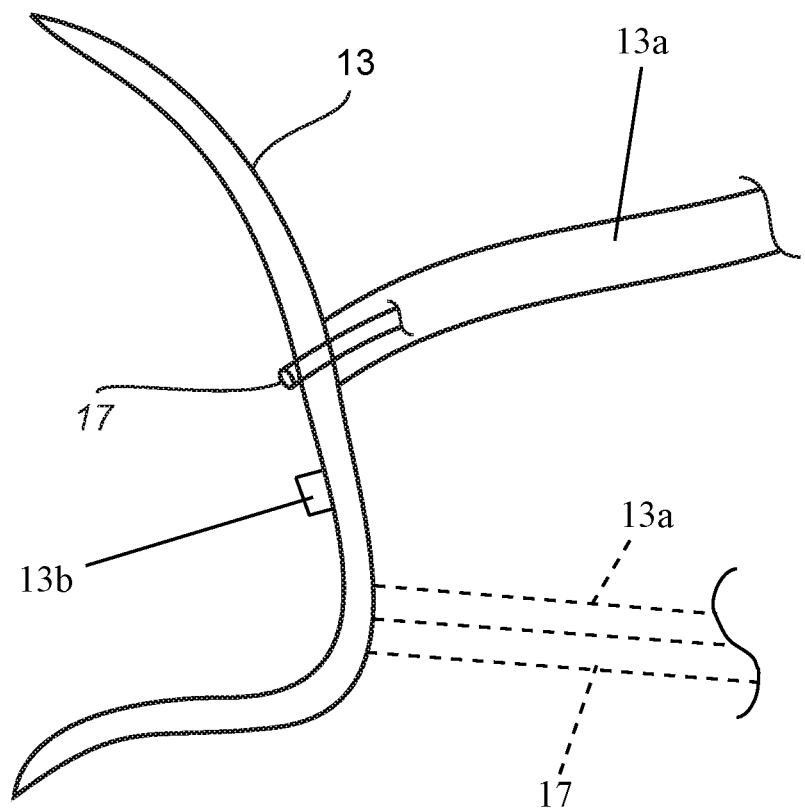
FIG. 4 shows connections to a mask 13 with oxygen delivery hose 17.

FIGS. 3 and 4 show a means of connecting the oxygen flow to the airflow inside the PAP machine and then delivery both airflow and oxygen to the mask using coaxial or co-linear tubing. Preferably, a conserver valve may deliver oxygen only when the patient inhales. This technique is used extensively in portable oxygen concentrators to reduce the total oxygen required to maintain requisite blood oxygenation. The conserver valve and associated circuitry typically responds to changes in the pressure sensed near the patient's nose or mouth.

FIG. 3 shows the oxygen concentrator components and PAP components inside the same housing. While this arrangement streamlines the system design and makes the system portable as a single unit, it may be desirable in some instances to build the PAP and oxygen concentrator as two separate modules that can be connected and operated as a single unit, or disconnected and operated independently. This allows the oxygen concentrator module to be used independently with a battery if the patient also requires oxygen therapy during waking hours. Also, if the patient requires oxygen with PAP during sleep for only a few days or weeks, the concentrator module can be decoupled and returned to the medical equipment provider when it is no longer needed. This reduces cost to the patient, and provides flexibility in use of the components.

Connectivity of Modules

If the PAP machine 10 and oxygen concentrator 11 are supplied as modules, the pieces must be easily connected and disconnected. In the case of the separate oxygen concentrator 11 it must be connected to a battery 126 for portable use. PAP machines 10 often operate at 24 volts DC (and sometimes at the local AC line voltage), which is supplied via an AC operated and separate "power cube" or power module, such as an AC to DC power conversion module 9. Operating at 24 volts (or any other low DC voltage) provides safety advantages and allows the PAP unit or machine 10 to be battery powered in the event of a power failure. In this case, the oxygen concentrator or oxygen concentrator module 11 can share the DC PAP power source. In a DC powered device the minimum necessary connections between the PAP machine 10 and the oxygen concentrator module 11 are the DC power connection and an oxygen connection to deliver oxygen from the oxygen concentrator module 11 to the PAP machine 10 and then to the mask 13. When the PAP module or machine 10 is powered on the oxygen concentrator module 11 is also powered on and produces a steady flow of oxygen to the conserver valve and then to the mask 13. It is a simple matter to make the two DC connections and the simple pneumatic connection. Mechanically connecting the PAP and oxygen concentrator modules 10, 11 strengthens and adds stability to the other functional connections.

Figure 5:
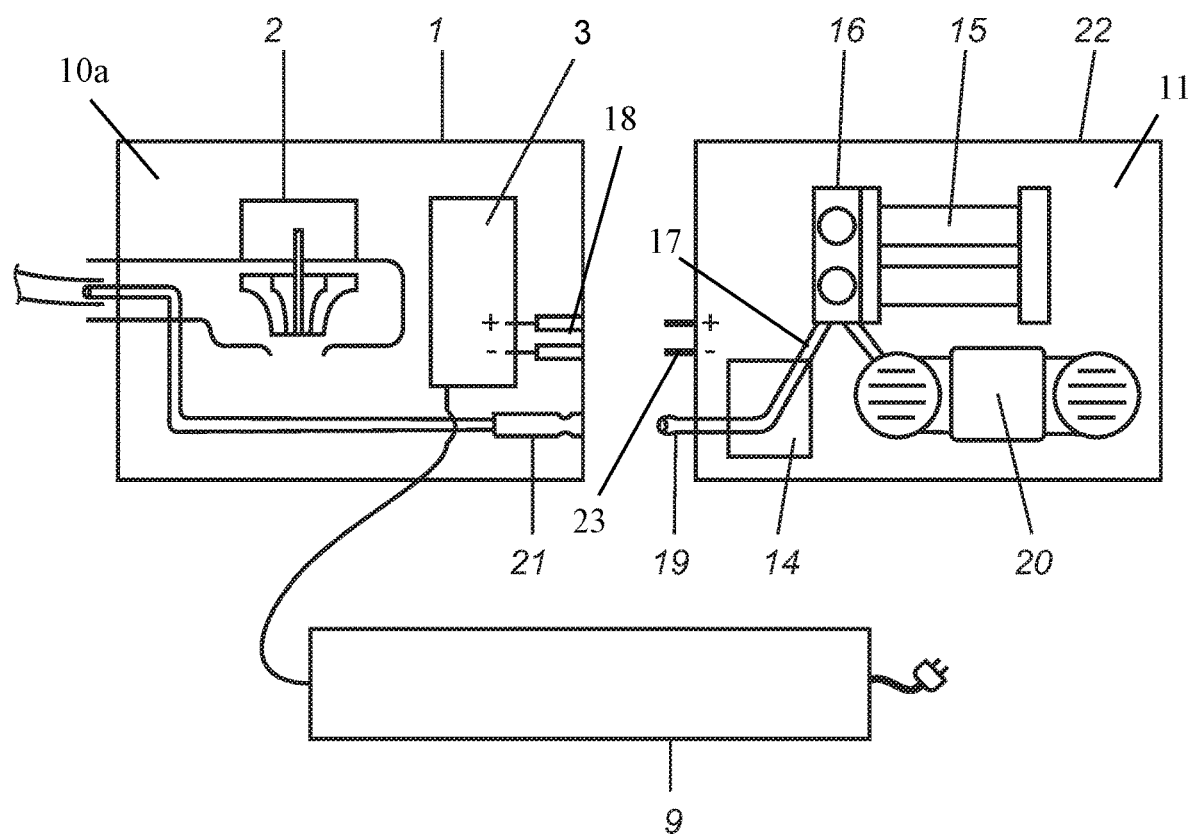
FIG. 5 illustrates one embodiment of a PAP device or system having a controllable flow generator 10a and an oxygen concentrator 22 designed for easy interconnection via connectors, including a DC in connector 18, an oxygen outlet 19, an oxygen inlet 21, and a DC out connector 23, wherein an AC-to-DC conversion module or AC-to-DC power conversion module 9 is shown.

As seen in FIG. 5, the PAP module or machine 10 may have female receptacles for both the electrical connections and the oxygen port. The oxygen concentrator module 11 has its own onboard electronics for PSA valve timing, compressor control and any other typical concentrator functions and the PAP machine or module 10 includes the blower 2, a circuit board 3, a pressure sensor 4, a temperature sensor 5, controls 6, a display 7, a humidity sensor 8 and a water tank 46. Active electronic noise cancellation may also be part of the electronic functions. Because the sieve module or cartridge 15 is user-replaceable, there may also be sensors for detection of sieve degradation. Sieve degradation leads to reduced oxygen purity and a warning indicator can alert the user to replace the sieve bed. If more information must be transferred between the PAP and oxygen concentrator modules 10, 11, additional electrical connections can be provided.

Figure 6:
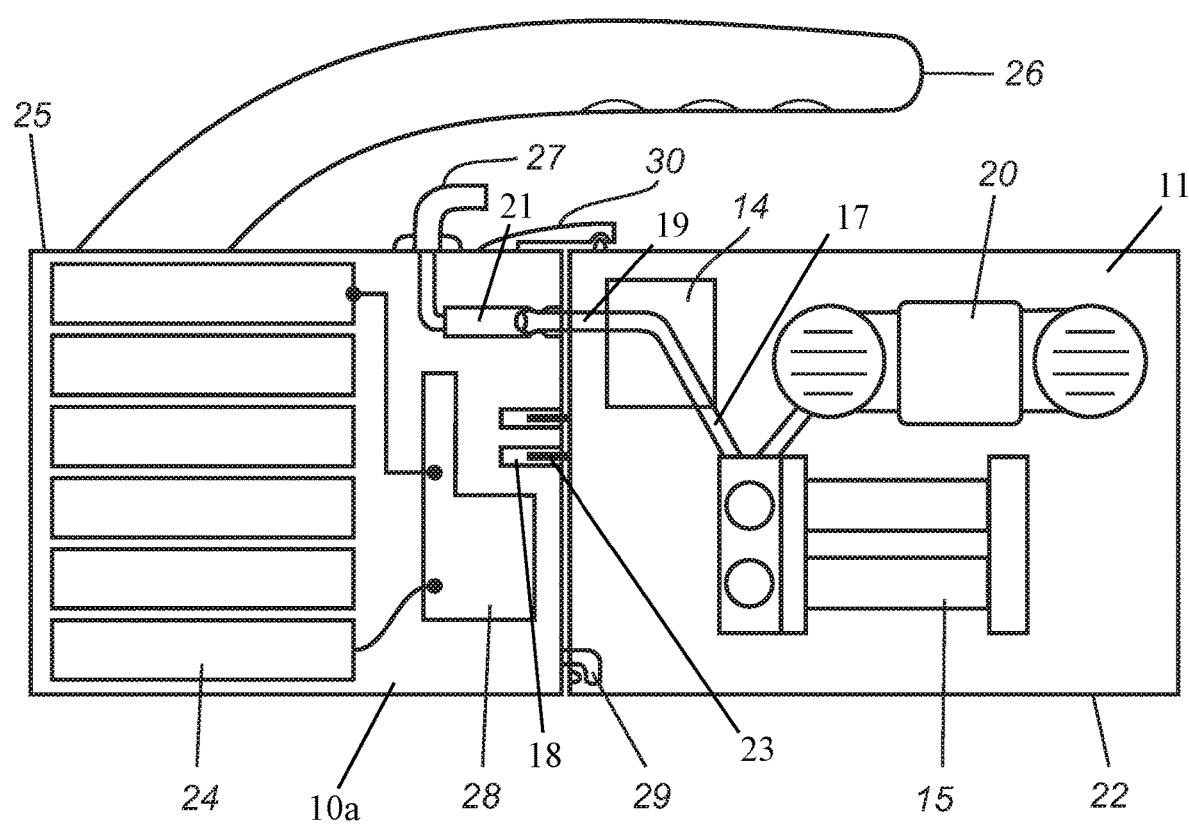
FIG. 6 shows one embodiment of a system with a specially designed oxygen concentrator 11 having a concentrator housing 22 and a controllable flow generator 10a with a battery housing 25, batteries 24, an oxygen fitting 27, battery circuitry 28, a mechanical connector 29, a clasp 30 and a handle 26 utilizing similar interconnects used to mate the battery to the oxygen concentrator.

If the oxygen module is to operate independently of the PAP device it must have its own power supply. FIG. 6 shows a possible design for the independent use of the concentrator module.

Figure 7:
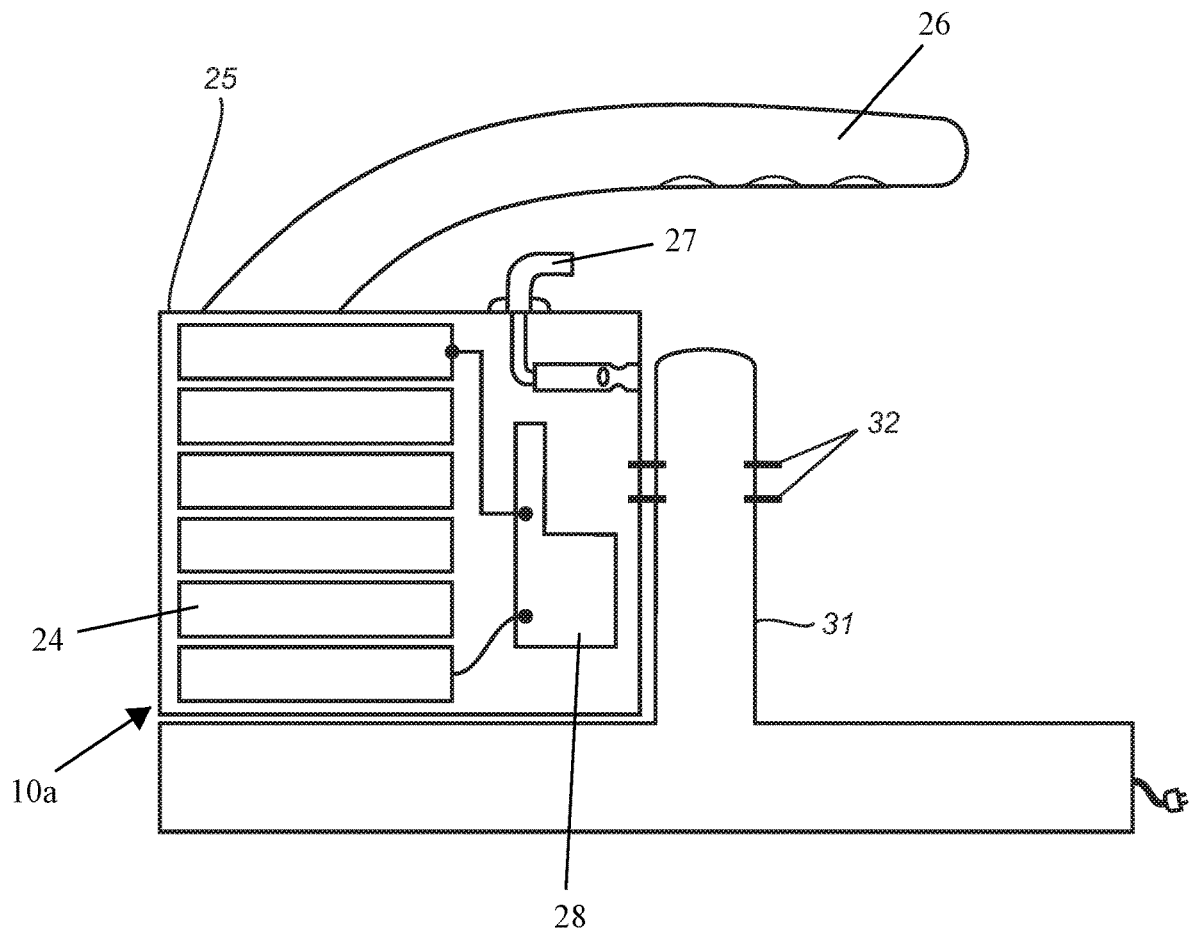
FIG. 7 illustrates one embodiment of a battery charger 31 with DC connectors 32 for the system that can accommodate two batteries.

FIG. 7 illustrates one embodiment of a battery charger. This allows the daytime battery to be charged while the PAP-concentrator is being used during sleep. The charger may be configured to charge one battery or multiple batteries.

Replacement Sieve Module

Suitable user-replaceable sieve modules useful for concentrating oxygen from ambient air (also referred to as "oxygen concentrators" and "pressure swing adsorption units") are described in U.S. Pat. Nos. 8,894,751, 9,199,055, 8,888,902, which are incorporated by reference in their entirety. The user-replaceable sieve modules may utilize any size molecular sieve, such as, for example, from 50 microns to 1000 microns. In certain preferred embodiments, beads may range in diameter from approximately 80 microns to 120 microns. In certain other preferred embodiments, the user-replaceable sieve modules contain less than 50 g of adsorbent material total. These small beads enable cycle times as fast as 2 Hertz and productivity in excess of 30 ml/minute/gram of adsorbent. This means that an adsorbent inventory of 25 grams can produce 750 ml/minute of oxygen, when utilized with a conserver 14, equates to over 2 liters per minute of oxygen. This flow rate is the commonly prescribed rate for both PAP adjunctive oxygen and daytime oxygen. The great advantage of the rapid cycle time is that oxygen concentrator technology can now be integrated into devices such as PAP and wound care devices without increasing the device footprint in an unreasonable amount. The only limiting factor is that the small adsorbent inventory means that performance may degrade from moisture contamination in 6 to 18 months, necessitating replacement of the adsorbent module. U.S. Pat. Nos. 8,894,751, 9,199,055, and 8,888,902 describe methods for user replacement of the sieve module much like a patient would replace a battery. The major component of the oxygen generation system is miniaturized, sieve lifetime is not an obstacle, and the small footprint of the PAP machine is retained. Larger sieve beads may be used but additional space would be required for the sieve module(s).

Figure 8A:
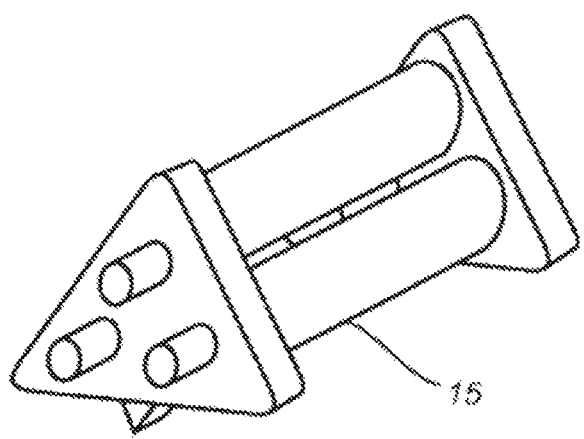
FIG. 8A shows a perspective view of the user-replaceable sieve cartridge (15) of one embodiment.
Figure 8C:
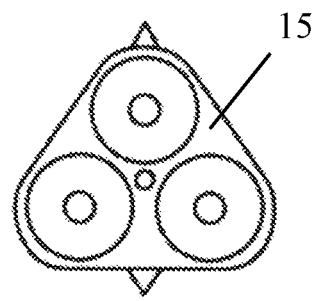
FIG. 8C shows an end view of the user-replaceable sieve cartridge 15 of one embodiment.
Figure 8D:
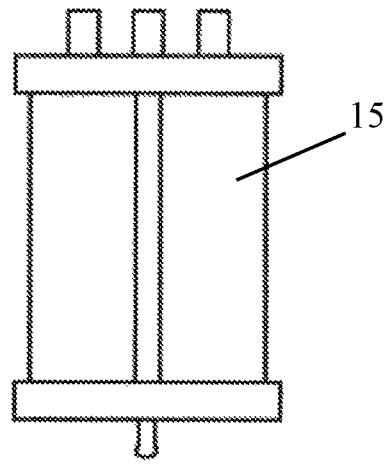
FIG. 8D shows a side view of the user-replaceable sieve cartridge 15 of one embodiment.
Figure 8B:
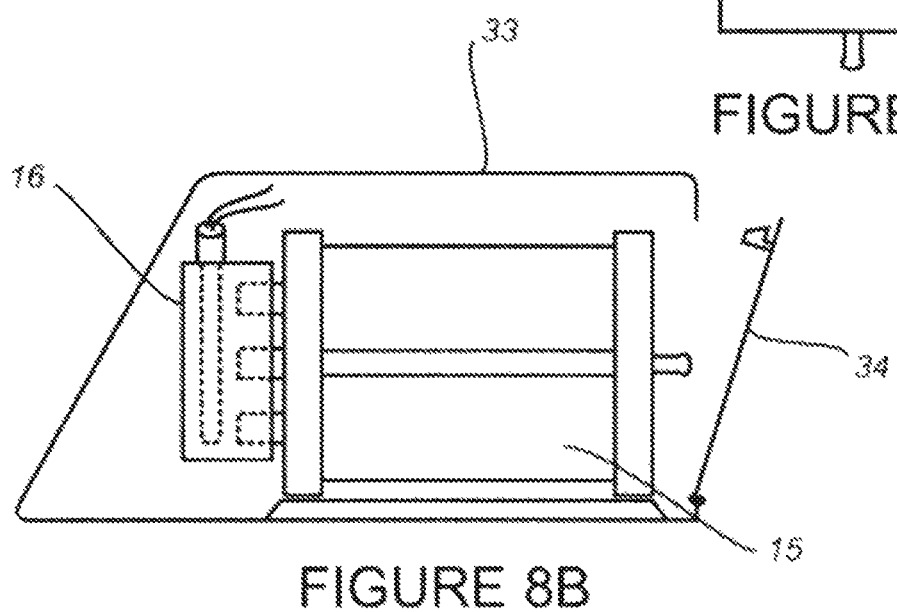
FIG. 8B illustrates one embodiment of the sieve cartridge 15 being located in a PAP housing 33 with an access door 34 and having valves and a manifold 16.

FIG. 8A illustrates an embodiment of a user-replaceable sieve module with two adsorbent columns, an oxygen reservoir, and an end block with the three pneumatic connections. The end block mates with a valve manifold. Guide rails for correct positioning of the module are also shown. These rails have associated grooves built into the concentrator case. FIG. 8B shows a door built into the end wall of the concentrator. This door has an associated clasp for easy opening and closing. The door provides access to the sieve module which can be removed and replaced without tools. The access door may be located on any wall of the device, including the wall normally obscured by the battery.

Figure 12:
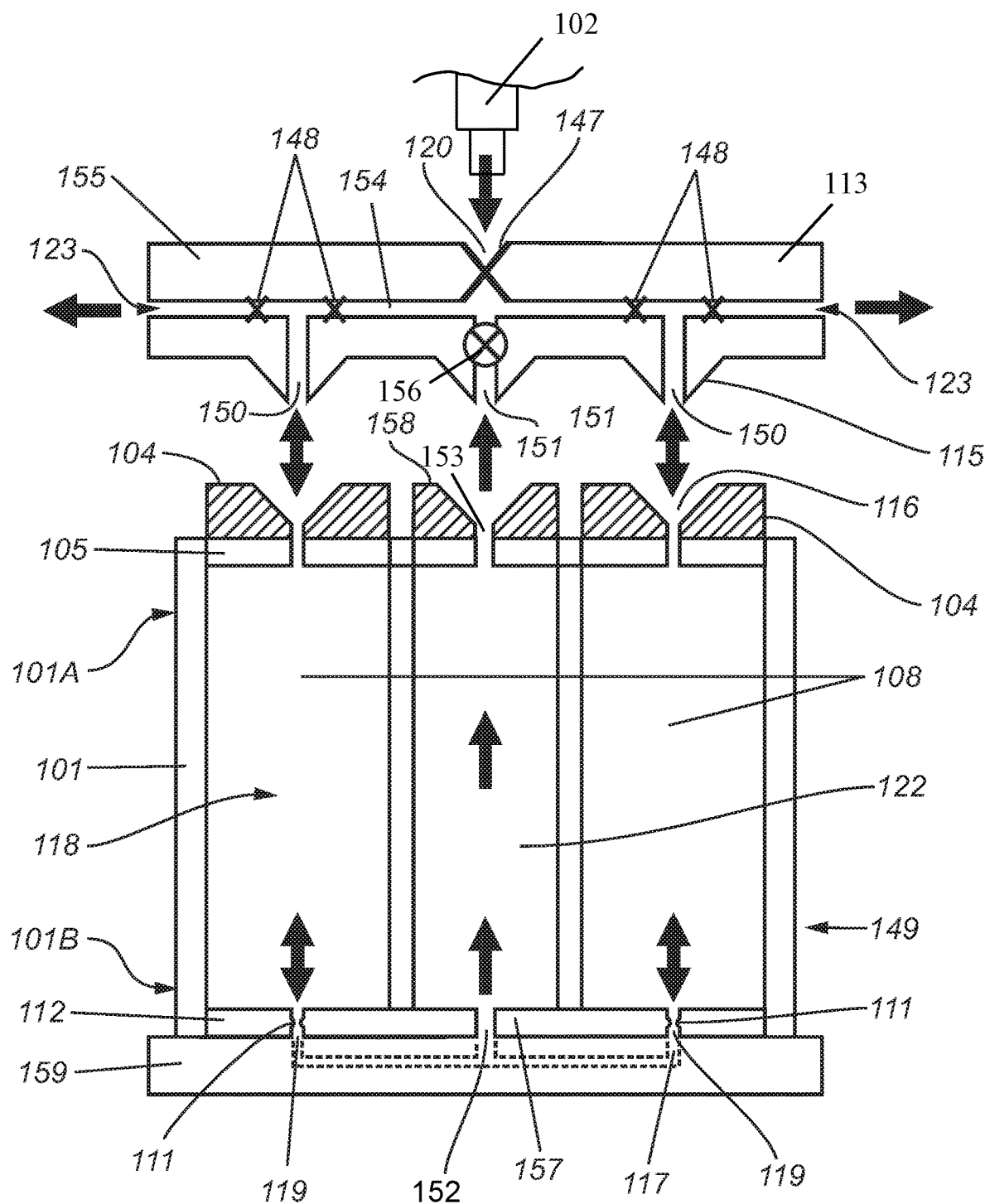
FIG. 12 is a cross-sectional view of the removable module 149 and the manifold 113 portions of a portable oxygen concentrator 11.
Figure 13:
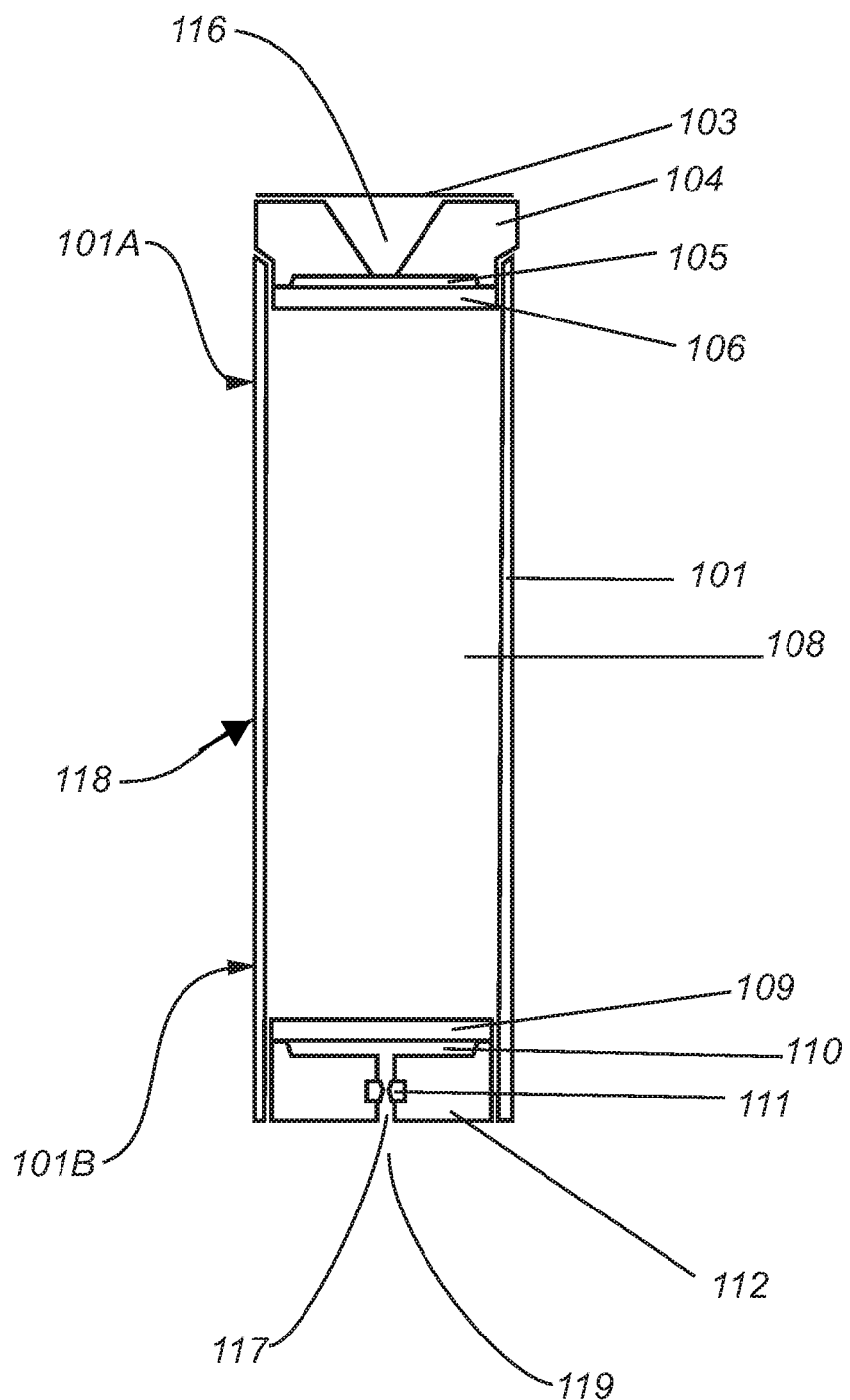
FIG. 13 is a vertical cross-section of one embodiment of the removable sieve cartridge 118 showing an optional rupture plate 103 covering the feed end plug 104 to seal the adsorbent bed 108 and prevent contamination, especially contamination from moisture, during storage prior to use.
Figure 14:
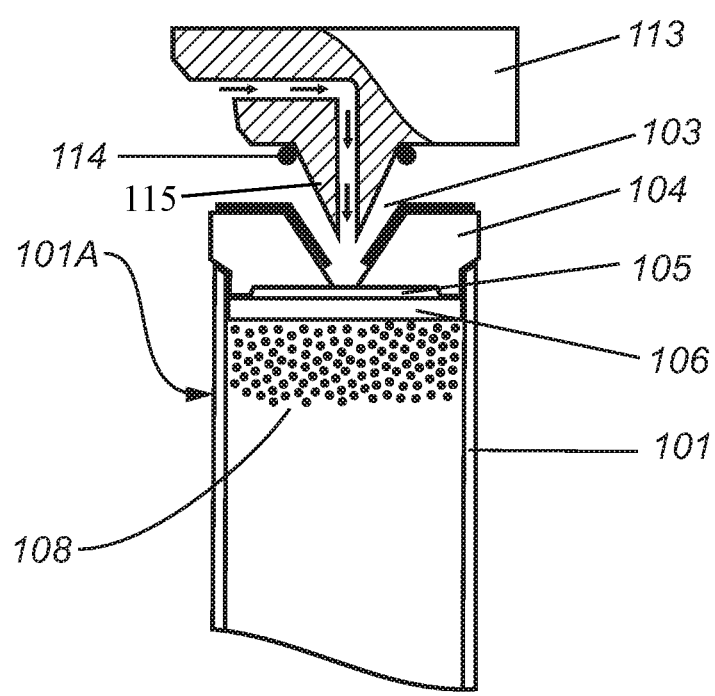
FIG. 14 shows one method of making pneumatic connections, the drawing being a vertical cross-section of a piercing mechanism 115 and module connections to the manifold 113 with the rupture plate 103 (shown after piercing by the piercing mechanism 115) and a seal 114.

FIG. 12 is a cross-sectional view of one embodiment of a removable module 149 and a manifold 113 portions of a portable oxygen concentrator 11 showing compressed air flow from a compressor 20.

The removable module 149 in the embodiment of FIG. 12 has two sieve cartridges 118. The cartridge 118 has a housing 101 having a feed end 101A and a product end 101B; at least one input port 116 for incoming air flow in said feed end 101A; a feed end plug 104; a diffusion channel 105 in said feed end 101A, an optional rupture plate 103 or other type of covering for said input port 116; and at least one adsorbent bed 108 contained in said housing 101, at least one output port 117 for an oxygen-enriched product flow in said product end 101B, and a product end plug 112 comprising a gas flow control orifice 111 and at least one collection channel 110. In certain embodiments, the adsorbent bed 108 comprises at least one molecular sieve material having an average particle size of about 60 µm to 180 µm and having a substantially spherical shape. The adsorbent bed 108 has an aspect ratio of length to diameter of less than about 6. Optionally the cartridge 118 has a fibrous pad in the input port 116, or the center feed hole 119 positioned at either end or both ends of said adsorbent bed 108.

The removable module 149 in the embodiment of FIG. 12 has at least one enriched-oxygen product tube 122, which has an input end plug 157; an oxygen input port 152 in said input end plug 157; an output end plug 158; an oxygen output port 153 in the output end plug 158; and an optional rupture plate 103 for the oxygen output port.

The removable module 149 in the embodiment of FIG. 12 has a product end block 159 has passageway 119 for transport of said oxygen-enriched product. Each cartridge 118 and the enriched-oxygen product tube 122 are connected to said product end block 159.

The portable oxygen concentrator in the embodiment of FIG. 12 also has a manifold 113 to control gas flow into and out of the removable sieve cartridge 118. The manifold 113 has a solid body 155 having a manifold passageway 154 for transporting fluid. Within the solid body 155, there is also a connection or passageway for compressed fresh air 120 from a compressor 102 to the manifold passageway 154 for transporting fluid with an optional 2-way compressor valve 147 within the connection or passageway for fresh air 120, a first connection or passageway 150 from the manifold passageway 154 to a sieve cartridge 118, a second connection or passageway 151 to the manifold passageway 154 from an oxygen-enriched product source or tube 122. Also, there is a valve 156 within the second connection or passageway 151. Two 3-way adsorbent bed valves 148 are found within the manifold passageway 154 for transporting fluids and are positioned on both sides of said first connection or passageway 150. The manifold passageway 154 leads to an exhaust port 123. The manifold or solid body 155 optionally has a piercing mechanism 115 or other type of pneumatic connector attached to the solid body 155 at the first connection and an optional piercing mechanism 115 or other type of pneumatic connector attached to the solid body 155 at the second connection with an associated seal 114.

FIG. 12 is a vertical cross-section of the cartridge 118 of the removable module 149 of one embodiment of the invention showing a rupture plate 103 covering the feed end plug 104 to seal the adsorbent bed 108 and prevent contamination, especially contamination from moisture, during storage prior to use. Other means may be employed to cover the sieve module ports. Housing 101 has a feed end 101A (which is also the exhaust end with respect to the nitrogen exhausted from the device) and a product end 101B (with respect to the oxygen-enriched product gas). In the feed end (i.e., where the compressed fresh air is received into removable module), there is at least one input port 116 for incoming air flow in said feed end, a feed end plug 104 (which can be made from such materials as polymers or lightweight metals), a diffusion channel 105, and an optional rupture plate 103 for said input port. In the product end (i.e., where one of the fluid flows in enriched in oxygen after passing through the adsorbent beds described herein), there is a product end plug 112 comprising a gas flow control orifice 111, at least one collection channel 110, and at least one passageway (center feed hole 119) for transport of said fluid product, and an optional rupture plate 103 for said output port 117. Housed within the removable module is at least one adsorbent bed 108 contained in said housing 101, wherein said adsorbent bed comprises at least one molecular sieve material having an average particle size of about 60 μm to 180 μm and having a substantially spherical shape. The adsorbent bed has an aspect ratio of length to diameter of less than about 6. Optionally, a fibrous pad 106, 109 may be positioned at either end of said adsorbent bed.

Compressed Air for the PSA Cycle

Oxygen concentrators operate using a process called pressure swing adsorption (PSA). It requires that air be provided under pressure (and sometimes under vacuum). Small compressors are used for this purpose and account for the majority of the power used by the system. Typical power requirements are about 40 to about 60 watts per liter per minute of oxygen produced. The compressor also contributes the majority of heat, noise, and vibration produced in the system.

Small oxygen concentrators often operate at noise levels ranging from about 35 to 50 dB. PAP devices are much quieter; some units operate at less than about 27 dB. PAP devices are designed to operate quietly because they are used in close proximity to the patient while the patient is sleeping. Pairing an oxygen concentrator with a PAP device requires that measures be taken to dramatically limit compressor noise. The inventors have devised several methods to accomplish this.

Figure 9:
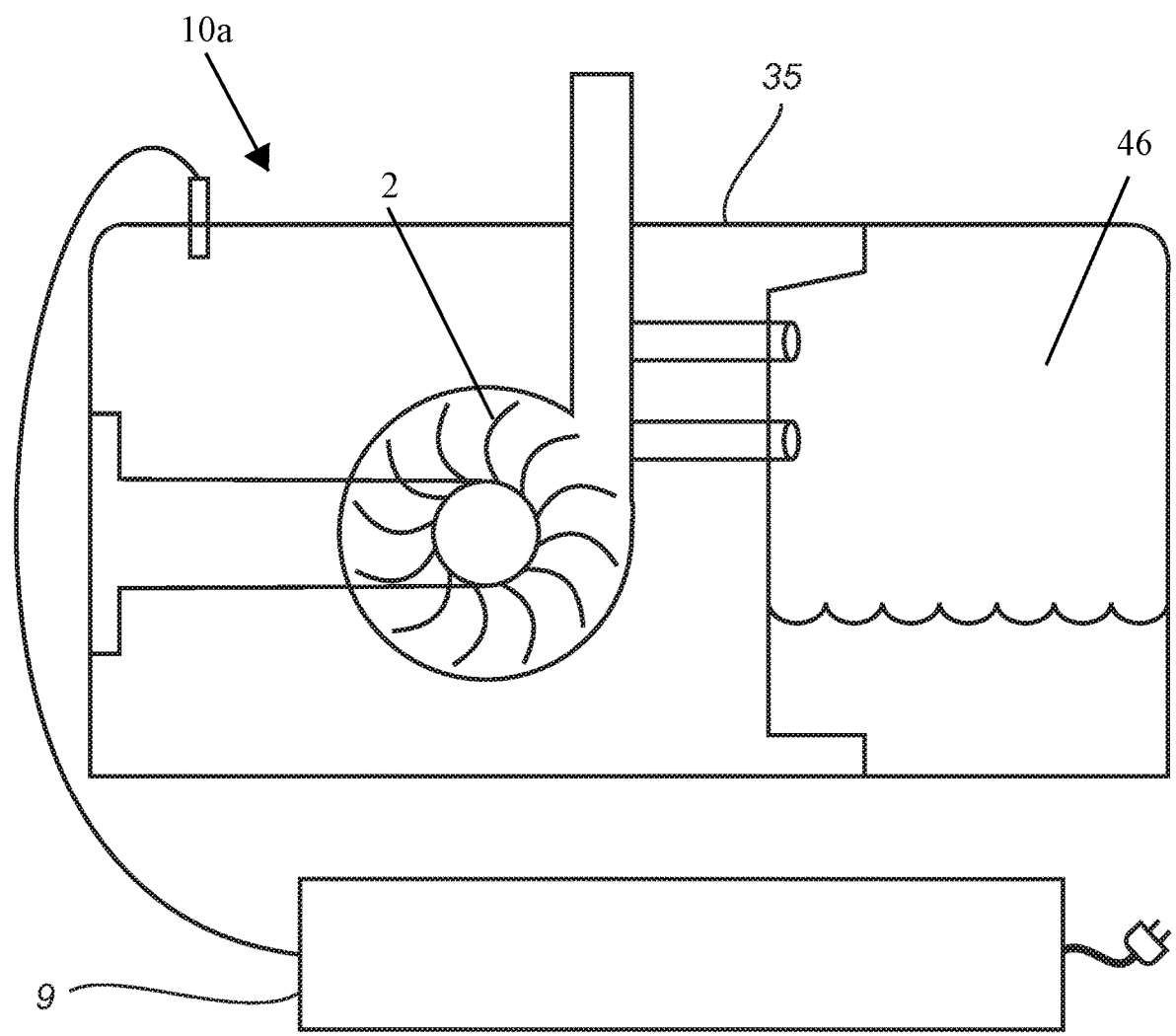
FIG. 9 shows a conventional or typical PAP machine or device with components 35 and an AC to DC power conversion module 9.
Figure 10:
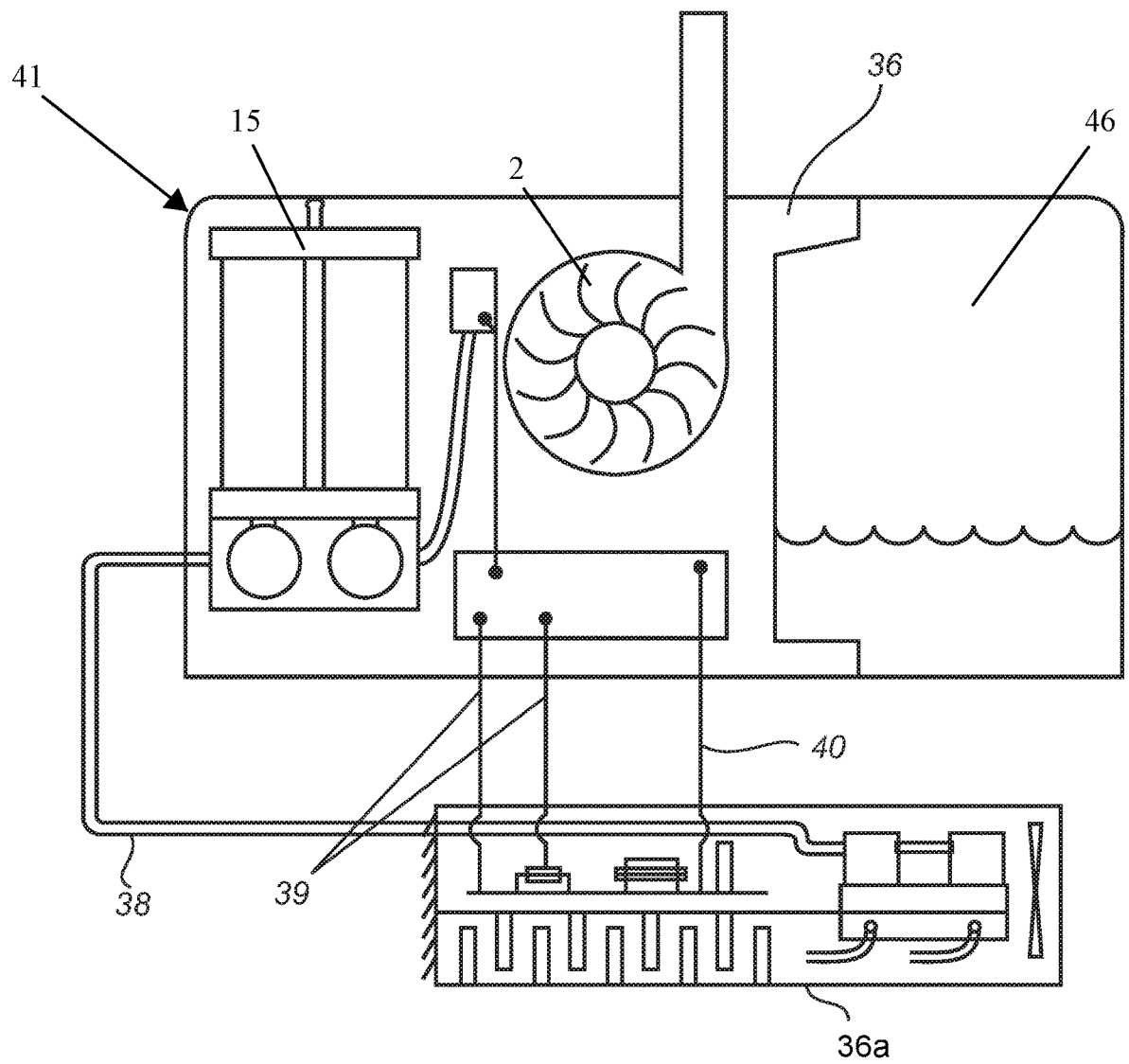
FIG. 10 shows the PAP machine with a sieve cartridge and valve manifold 36 included and a power supply 36a with integrated compressor and electrical connections including a DC cable 39 and a compressor speed control signal cable 40 and a pneumatic comprised of a compressed air delivery hose 38 that interconnects the sieve module 15 and the compressor and power supply 36a in one embodiment of the invention.
Figure 11:
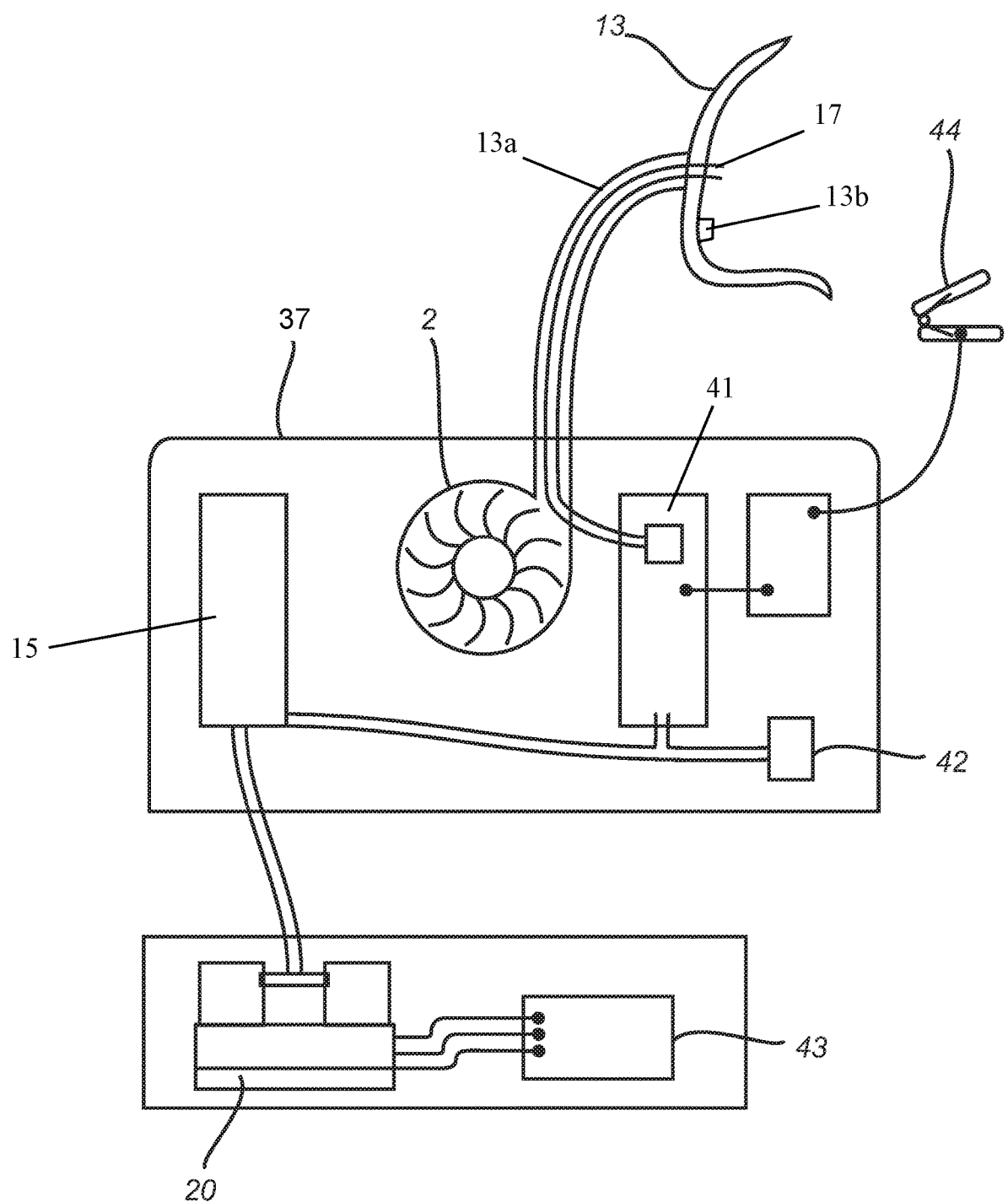
FIG. 11 shows the PAP device or system in one embodiment of the invention with comprised of a power supply with integrated compressor, muffler, fan, and compressor control circuitry 37 having an integrated oxygen producing module and reservoir 41 having the blower 2, an oxygen reservoir pressure sensor 42 and an oximetry sensor 44 and separate power module with compressor 20 and compressor speed control circuit or board 43.

The first method is for oxygen that is integrated directly into the PAP device. As stated earlier, PAP devices are often powered by an AC/DC power cube that has a cord to connect to the AC outlet and another low voltage DC cord which then connects to the PAP machine. Each of these cords may be 3-4 feet in length. The power cube typically sits on the floor near the AC wall outlet. The first noise mitigation technique is to locate the compressor in a housing that also holds the power cube. This keeps the compressor at a distance from the patient, at a lower elevation, and in housing that has room for insulation, vibration damping, silencers, and baffles. A length of pneumatic tubing runs parallel to the DC power cord connects the compressor outlet to the PSA module in the PAP device. The electronic circuitry which drives the compressor, typically a DC-to-polyphase converter, is also located in the power cube/compressor module. An analog or digital signal may originate in the PAP device in response to a setting or electronic control and is delivered to the compressor driver circuit on a conductor(s) which also runs parallel to the compressed air tube and low voltage DC cord. So the PSA sieve module and valve control circuitry is located in the PAP housing, the compressor is located with power cube and the result is a low noise PAP machine with oxygen producing capability that has components that are only slightly increased in size and weight and thus may fit into the same travel case as the original PAP device. FIG. 9 illustrates how the original PAP components are arranged and FIG. 10 shows how they are modified to accommodate the added oxygen concentrator components.

The second noise mitigation method is to employ a balanced linear compressor or a sliding vane compressor. These compressors can have significantly lower noise and vibration signatures. These compressors can be used in the power cube space, integrated into the PAP unit, or as a component of a separate concentrator module. Because the user-replaceable sieve module with 100 micron beads is approximately 6-8 cubic inches smaller than conventional sieve modules having the same 800 ml/min output, additional space is available for sound dampening. Most compressor noise emanates from the intake (the outlet is silenced by the sieve beds). The additional available space can be used for complex intake silencers. These may be used in any of the PAP-oxygen concentrator designs described here.

The third noise mitigation technique is to use electronic active noise cancellation technology (ANC). This provides audio signals that can cancel noise by out-of-phase power relationships that smooth audio peaks. This technique can be used regardless of the location of the compressor [and in combination with other techniques].

Oximetry Feedback Control for Oxygen Delivery

Oxygen delivery rates may be controlled by certain sensor or by the patient or by physician-selected parameters. Some of these are listed below but this list is not all inclusive and it is understood that other feedback parameters may be utilized to optimize the effect of oxygen delivery depending upon the specific situation.

finger oximetry sensor 44
CO2 breath analysis (luminescence quenching)
feedback to 02 delivery rate (PSA system)
respiratory arrhythmia events
physician-selected feedback algorithms Reporting, Respiratory Arrhythmia, Low Blood 02, Adherence, Device Malfunctions PAP machines may have communications capabilities that can report a variety of conditions, rates, and occurrences to the respiratory physician, caregiver, nursing home, and equipment provider.

For the both CPAP/BPAP oxygen concentrator combination systems described herein, it is contemplated that all embodiments could have WIFI, RF, LTE, Bluetooth, LAN, cellular or other tethered or non-tethered communications capabilities. Such communication capabilities can allow for active or passive transfer of information, tracking, instructions or processing of information. A software application on a user's phone is contemplated that can communicate with the system such that the user or a remote user of the application can review information provided by the system. Such information can include, but is not limited to: system identification, user identification, humidity level, air contaminants, time and location, power status, status of sieve beds, amount of oxygen flow, oximeter measurements, pulse, breathing rate, blood pressure, air pressure, room temperature and other relevant patient and environmental information. Ideal situations would include a parent being able to remotely monitor a newborn infant or a caregiver being able to remotely review via the application the health and system information. It is further anticipated that in another embodiment, the remote user interface can be more active, allowing the user or health provider to remotely access the CPAP/BPAP oxygen concentrator system to remotely program either the CPAP/BPAP, oxygen concentrator or both.

In addition to active or passive transfer of instructions or information, the communications system would be integrated such that the separate systems would communicate between each other and with accessories. For example, as described above, finger oximetry sensor 44 is utilized with current PAP devices. The integrated communication contemplated in this patent application would provide the ability of the oximeter device or sensor 44 to communicate $O_2$ levels to either a software program within the PAP-oxygen concentrator system or to a remote program where such $O_2$ information would be evaluated for blood $O_2$ levels. In one embodiment, the O₂ evaluation program would then send a signal to the oxygen concentrator to maintain, decrease or increase the volume of O₂ in response to parameters established in the program.

It is also recognized that for all embodiments described herein, the invention is applicable to a CPAP, BPAP, or an auto PAP device.

It will be apparent to those skilled in the art that various modifications and variations can be made in the present invention and specific examples provided herein without departing from the spirit or scope of the invention. Thus, it is intended that the present invention cover the modifications and variations of this invention that come within the scope of any claims and their equivalents.

When ranges are used herein for physical properties, such as molecular weight, or chemical properties, such as chemical formulae, all combinations, and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

| Component Number | Component Name |
|---|---|
| 1 | Housing |
| 2 | Blower |
| 3 | Circuit board |
| 4 | Pressure sensor |
| 5 | Temperature sensor |
| 6 | Controls |
| 6a | Wireless transmitter |
| 6b | Wireless receiver |
| 7 | Display |
| 8 | Humidity sensor |
| 9 | AC to DC power conversion module |
| 10 | PAP machine |
| 11 | Oxygen concentrator |
| 12 | Oxygen to PAP connection |
| 13 | Mask |
| 13a | Gas Deliver Tube |
| 13b | Sensor |
| 14 | Conserver |
| 15 | Replaceable sieve cartridge |
| 16 | Valves and manifold |
| 17 | Oxygen hose |
| 18 | DC connector(s), in |
| 19 | Oxygen outlet |
| 20 | Compressor |
| 21 | Oxygen inlet |
| 22 | Concentrator housing |
| 23 | DC Connection, out |
| 24 | Batteries |
| 25 | Battery housing |
| 26 | Handle |
| 27 | Oxygen fitting |
| 28 | Battery circuitry |
| 29 | Mechanical connector |
| 30 | Clasp |
| 31 | Battery charger |
| 32 | DC connectors |
| 33 | PAP machine with oxygen housing |
| 34 | Replaceable sieve cartridge door |
| 35 | Typical PAP machine, components |
| 36 | PAP machine with integrated sieve cartridge and manifold |

-continued

| Component Number | Component Name |
|---|---|
| 37 | Power supply with integrated compressor, muffler, fan, and |
| 38 | Compressed air delivery hose |
| 39 | DC cable |
| 40 | Compressor speed control signal cable |
| 41 | Oxygen reservoir |
| 42 | Oxygen reservoir pressure sensor |
| 43 | Compressor speed control board |
| 44 | Oximetry sensor |
| 45 | Oximetry to conserver electronic interface |
| 46 | Water tank |
| 50 | Therapeutic Cartridge |
| 51 | Receptacle |
| 101 | Housing |
| 101A | Feed end of housing |
| 101B | Product end of housing |
| 102 | Compressor |
| 103 | Rupture plate |
| 104 | Feed end plug |
| 105 | Diffusion channel |
| 106 | Fibrous pad |
| 107 | Pre-weakened pattern |
| 108 | Adsorbent bed |
| 109 | Fibrous pad |
| 110 | Collection channel |
| 111 | Gas flow control orifice |
| 112 | Product end plug |
| 113 | Manifold |
| 114 | Seal |
| 115 | Piercing mechanism |
| 116 | Input port |
| 117 | Output port |
| 118 | Cartridge |
| 119 | Center feed hole |
| 120 | Passageway for compressed fresh air |
| 122 | Enriched oxygen product tube |
| 123 | Exhaust port |
| 126 | Battery cell |
| 147 | 2-way compressor valve |
| 148 | 3-way adsorbent bed valve |
| 149 | Removable module |
| 150 | Passageway to/from cartridge |
| 151 | Passageway from enriched-oxygen product tube 122 |
| 152 | Oxygen input port in enriched oxygen product tube 122 |
| 153 | Oxygen output port in enriched oxygen product tube 122 |
| 154 | Manifold passageway |
| 155 | Solid body |
| 156 | Valve |
| 157 | Input end plug in enriched-oxygen product tube 122 |
| 158 | Output end plug in enriched-oxygen product tube 122 |
| 159 | Product end block |

What is claimed is:

1. A positive airway pressure system, comprising:
a controllable flow generator operable to provide breathable gas at a treatment pressure; wherein said treatment pressure is above atmospheric pressure, the controllable flow generator including an oxygen inlet;
a gas delivery tube coupled to said controllable flow generator;
a controllable oxygen concentrator device operable to provide oxygen-enriched gas, the controllable oxygen concentrator device including an oxygen outlet, the oxygen outlet interconnected to the oxygen inlet for providing concentrated oxygen from the controllable oxygen concentrator device to the controllable flow generator, wherein said controllable oxygen concentrator device comprises at least one user-replaceable sieve cartridge comprising less than about 50 g adsorbent, the controllable flow generator directly interconnected to the controllable oxygen concentrator by connectors and removable from the controllable oxygen concentrator without tools, the controllable flow generator interconnected to the controllable oxygen concentrator by a clasp on the controllable flow generator that is releasably interconnectable to a counterpart mechanical connector on the controllable oxygen concentrator such that the combined controllable flow generator and the controllable oxygen concentrator are portable so that patients may be mobile and conveniently travel;

an enriched gas delivery tube coupled to said controllable oxygen concentrator device, the enriched gas delivery tube extending from the sieve cartridge to the oxygen inlet when the connectors connect the controllable flow generator to the controllable oxygen concentrator, the enriched gas delivery tube extending through the controllable flow generator to the gas delivery tube;

a patient mask coupled to said gas delivery tube to receive breathable gas from said flow generator and to provide said gas, at approximately the treatment pressure, to an airway of a patient, the combined gas delivery tube and the enriched gas delivery tube terminating in the patient mask, the enriched gas delivery tube connected to a conserver valve to deliver the oxygen-enriched gas only when the patient inhales and terminating in the patient mask to minimize dilution of the oxygen-enriched gas during a patient's inhalation;

a controller operable to receive an input signal and to control the magnitude of said treatment pressure provided by said flow generator;

an oximetry sensor in communication with the controller and configured to sense a blood oxygen saturation level of the patient during operation of the controllable oxygen concentrator device; and a sensor to detect patient respiratory airflow and to generate an airflow signal, the airflow signal and the blood oxygen saturation level being transmitted to the controller, the controller configured to send a signal to the controllable oxygen concentrator to one of maintain, decrease, and increase a volume of oxygen based on the airflow signal and the blood oxygen saturation level.

2. A positive airway pressure system of claim 1, wherein at least a portion of said gas delivery tube and at least a portion of said enriched gas delivery tube are co-axially oriented, as a tube within a tube.

3. A positive airway pressure system of claim 1, wherein a central axis of at least a portion of said gas deliver tube and a central axis of at least a portion of said enriched gas delivery tube are substantially parallel.

4. A positive airway pressure system of claim 1, further comprising:
at least one battery.

5. A positive airway pressure system of claim 4, further comprising:
a charger for said at least one battery.

6. A positive airway pressure system of claim 1, further comprising:
at least one AC to DC power supply.

7. A positive airway pressure system of claim 1, further comprising:
a AC to DC power supply for said controllable flow generator.

8. A positive airway pressure system of claim 1, further comprising:
a AC to DC power supply for said controllable oxygen concentrator device.

9. A positive airway pressure system of claim 1, further comprising:
a conserver.

10. A positive airway pressure system of claim 1, wherein said controllable oxygen concentrator device comprises a linear compressor.

11. A positive airway pressure system of claim 1, further comprising:
a wireless transmitter or receiver or both a transmitter and receiver.

12. A positive airway pressure system of claim 1, further comprising:
a receptacle for a user-replaceable therapeutic cartridge.

13. A positive airway pressure system of claim 1, further comprising:
a user-replaceable therapeutic cartridge; and
a receptacle for said user-replaceable therapeutic cartridge.

14. A positive airway pressure system of claim 1, wherein said system weighs less than about 10 pounds.

15. A positive airway pressure system of claim 1, wherein said user-replaceable sieve cartridge comprises at least two adsorbent beds.

16. A positive airway pressure system of claim 1, wherein a delivery rate of said oxygen-enriched gas is controlled by a medical professional, programmed into said system, dependent upon a breath analysis, dependent upon the blood oxygen saturation level transmitted to the controller, dependent upon a respiratory arrhythmia event, or a combination thereof.

17. The positive airway pressure system of claim 1, wherein a central axis of the gas delivery tube and a central axis of the enriched gas delivery tube are substantially parallel forming a dual, side-by-side lumen.

18. A positive airway pressure system, comprising:
a first module comprising:
a controllable flow generator operable to provide breathable gas at a treatment pressure;
wherein said treatment pressure is above atmospheric pressure;
a gas delivery tube coupled to said controllable flow generator;
a patient mask coupled to said gas delivery tube to receive breathable gas from said flow generator and to provide said gas, at approximately the treatment pressure, to an airway of a patient;
a controller operable to receive an input signal and to control the magnitude of said treatment pressure provided by said flow generator; and
a sensor to detect patient respiratory airflow and to generate an airflow signal to said controller;
a second module;
wherein said second module is a battery or a charger; and
a third module comprising:
a controllable oxygen concentrator device operable to provide oxygen-enriched gas at a blood oxygen saturation level and an airflow level, the controllable oxygen concentrator device comprises at least one user-replaceable sieve cartridge;
an enriched gas delivery tube coupled to said controllable oxygen concentrator device, a conserver valve, and said controllable flow generator, the conserver valve configured to deliver the oxygen-enriched gas only when the patient inhales, the gas delivery tube connected to the enriched gas delivery tube and being separate from the enriched gas delivery tube, the combined gas delivery tube and the enriched gas delivery tube terminating in the patient mask to minimize dilution of the oxygen-enriched gas during a patient's inhalation such that the controllable flow generator and the controllable oxygen concentrator may be operated to independently provide the breathable gas at the treatment pressure or the oxygen enriched gas to the patient;

wherein said third module is mateable with said first module, said second module, or both said first module and said second module, the first module including a DC in connector and an oxygen inlet, the third module including a DC out connector and an oxygen outlet, the DC in connector mated to the DC out connector and the oxygen inlet mated to the oxygen outlet when the first module is mated to the third module; and a remote user interface in communication with the controllable flow generator and the controllable oxygen concentrator device, the remote user interface receiving the airflow signal, the remote user interface configured for remote access of the controllable flow generator and the controllable oxygen concentrator device to adjust the treatment pressure and the blood oxygen saturation level.

* * * * *